US008157779B2

(12) United States Patent
Williams

(10) Patent No.: US 8,157,779 B2
(45) Date of Patent: Apr. 17, 2012

(54) CONTOURED AND SHAPED FEMININE SANITARY DEVICE

(76) Inventor: Jacquelyn Lowden Williams, Temecula, CA (US)

( * ) Notice: Subject to any disclaimer, the term of this patent is extended or adjusted under 35 U.S.C. 154(b) by 0 days.

(21) Appl. No.: 11/950,652

(22) Filed: Dec. 5, 2007

(65) Prior Publication Data

US 2008/0091161 A1     Apr. 17, 2008

Related U.S. Application Data

(63) Continuation of application No. 11/257,275, filed on Oct. 24, 2005, now abandoned.

(60) Provisional application No. 60/638,879, filed on Dec. 22, 2004.

(51) Int. Cl.
*A61F 13/15* (2006.01)

(52) U.S. Cl. ........... 604/385.101; 604/358; 604/378; 604/379; 604/380; 604/385.01; 604/385.03; 604/385.04; 604/385.12; 604/385.16; 604/385.17

(58) Field of Classification Search ............ 604/358, 604/378, 385.01, 385.03, 385.12, 385.16, 604/385.17, 379, 380, 385.04, 385.101
See application file for complete search history.

(56) References Cited

U.S. PATENT DOCUMENTS

| | | | | |
|---|---|---|---|---|
| 3,441,025 A * | 4/1969 | Ralph | | 604/398 |
| 4,490,147 A | 12/1984 | Pierce | | |
| 4,536,181 A * | 8/1985 | Cook | | 604/387 |
| 4,678,464 A * | 7/1987 | Holtman | | 604/385.03 |
| 4,753,644 A * | 6/1988 | Cottenden et al. | | 604/378 |
| 5,127,911 A | 7/1992 | Baharav | | |
| 5,545,156 A * | 8/1996 | DiPalma et al. | | 604/385.23 |
| 5,599,337 A * | 2/1997 | Mccoy | | 604/385.01 |
| 5,624,421 A * | 4/1997 | Dabi et al. | | 604/378 |
| 5,624,423 A * | 4/1997 | Anjur et al. | | 604/385.21 |
| 6,059,763 A | 5/2000 | Brown | | |
| D426,887 S * | 6/2000 | Rubio | | D24/125 |
| D440,308 S * | 4/2001 | Ibrahim | | D24/125 |
| 6,313,371 B1 * | 11/2001 | Conant et al. | | 604/359 |
| 6,325,786 B1 * | 12/2001 | Bjorklund et al. | | 604/385.01 |
| 6,395,956 B1 * | 5/2002 | Glasgow et al. | | 604/378 |
| 6,398,770 B1 * | 6/2002 | Drevik | | 604/385.01 |
| 6,475,199 B1 * | 11/2002 | Gann et al. | | 604/385.01 |
| 6,492,574 B1 * | 12/2002 | Chen et al. | | 604/378 |
| 6,620,144 B1 * | 9/2003 | Glasgow et al. | | 604/385.17 |
| 6,652,503 B1 * | 11/2003 | Bradley | | 604/385.17 |
| 6,669,675 B2 * | 12/2003 | Lipman et al. | | 604/329 |
| 6,685,689 B1 * | 2/2004 | Ronnberg | | 604/385.28 |
| 6,887,224 B2 * | 5/2005 | Rubio | | 604/385.03 |
| 6,908,456 B1 * | 6/2005 | Drevik | | 604/385.04 |
| 6,929,629 B2 * | 8/2005 | Drevik et al. | | 604/385.31 |
| 7,179,247 B2 * | 2/2007 | Mizutani et al. | | 604/385.101 |
| 7,195,619 B2 * | 3/2007 | Manasek | | 604/385.01 |
| 7,368,627 B1 * | 5/2008 | Widlund | | 604/378 |
| 2004/0254556 A1 | 12/2004 | Brisebois | | |

* cited by examiner

*Primary Examiner* — Tatyana Zalukaeva
*Assistant Examiner* — Ginger T Chapman
(74) *Attorney, Agent, or Firm* — Loza & Loza LLP; Heidi L. Eisenhut

(57) ABSTRACT

A contoured and shaped feminine sanitary device (10) comprising a substantially fluid-impermeable bottom layer (26), a substantially fluid-absorbent core (24), and a substantially fluid-permeable top layer (28), with at least one raised area (18) and at least one of back or front extensions (14,16) for facilitating and enhancing fluid absorption in certain areas and during certain activities.

17 Claims, 2 Drawing Sheets

CONTOURED AND SHAPED FEMININE SANITARY DEVICE

RELATED APPLICATIONS

The present continuation patent application is related to and claims priority benefit of an earlier-filed non-provisional patent application of the same title, Ser. No. 11/257,275, filed Oct. 24, 2005 now abandoned, and an even earlier-filed provisional patent application titled FEMININE SANITARY DEVICE, Ser. No. 60/638,879, filed Dec. 22, 2004. The identified earlier-filed applications are hereby incorporated by reference into the present application.

BACKGROUND OF THE INVENTION

1. Field of the Invention

The present invention relates broadly to feminine sanitary napkins, pads, or other similar devices. More particularly, the present invention concerns a contoured and shaped feminine sanitary device comprising a substantially fluid-impermeable bottom layer, a substantially fluid-absorbent core, and a substantially fluid-permeable top layer, with at least one raised area and at least one of back or front extensions for facilitating and enhancing fluid absorption in certain areas and during certain activities.

2. Description of the Prior Art

Feminine sanitary napkins or pads are well-known in the prior art as comprising a fluid-absorbent core interposed between a fluid-impermeable backing and a fluid-permeable cover for placement against the female genital area to absorb bodily fluid during menstruation. Unfortunately, such prior art pads generally function best when the user is in a substantially vertical position, i.e., standing or sitting upright such that the natural flow of such fluid is directly into the pad. When the user is reclining or laying in a supine, prone, or side position, fluid can avoid absorption by the prior art pad by flowing along the contours of the body to an area that is unprotected by the prior art pad. Thus, for example, when the user is sleeping, substantial amounts of fluid may avoid being absorbed by the prior art pad and may ultimately contact and stain the user's garments or bedcoverings.

U.S. Pat. No. 6,059,763 discloses a feminine sanitary pad having a "gluteal pad extending from an end of the horizontally extending base pad for providing additional absorption of backward spillage occurring when a woman lies in a horizontal position." The gluteal pad takes the form of a wedge for placement between the lower buttocks. Unfortunately, such a wedge works to absorb spillage only when the user lies in a supine horizontal position such that the spillage flows rearwardly. The gluteal wedge does not work to absorb spillage when the user lies in a prone horizontal position such that the spillage flows forwardly. Similarly, the gluteal wedge does not work to absorb spillage when the user lies on her left or right side such that the spillage flows sidewardly. Thus, the gluteal wedge protects the user in only one of the four basic sleeping positions. The gluteal wedge suffers from a number of additional disadvantages, including, for example, that it only absorbs fluid flowing between the buttocks and not fluid flowing over the buttocks, and that the overly-intrusive wedge shape may be unduly uncomfortable or otherwise disagreeable for some women.

It is known to combine a feminine sanitary pad with a tampon in order to increase the amount of absorption of fluids and to reduce spillage. Unfortunately, tampons, while generally effective, pose health risks for women. Toxic shock syndrome (TSS) is a rare but potentially deadly disease. Using tampons of any absorbency greatly increases a woman's risk of contracting TSS. A sudden high fever, diarrhea, fainting, bloodshot eyes, and a rash are some of the most severe symptoms of TSS. In order to reduce the risk of contracting TSS, doctors suggest the use of feminine sanitary pads, but as mentioned, prior art pads by themselves suffer from a number of problems and disadvantages.

U.S. Pat. No. 4,490,147 discloses a sanitary device which claims to be more absorbent than conventional pads due to the placement of parallel, elongated, cylindrical structures and a swellable sponge between the base and the cover layers. One embodiment comprises three cylindrical pads in a triangle formation, resulting in a heightened area throughout much of the length of the pad. One disadvantage of this single, elongated wedge is discomfort for the user because it does not and cannot conform to the natural contours of the female genital area. In addition, there is still the possibility of spillage or leakage if the user lies in a horizontal position such that the fluid flows either forward toward the pelvic area, rearward toward the buttocks, or toward the sides of the pad.

Prior art adult diapers are also well-known and can be used as an extreme solution to the problem of containing fluid flow. Adult diapers may contain elastic along the sides and are padded for fluid absorption along the entire interior to provide for maximum protection. Even though the risk of leakage is very low, adult diapers may not provide sufficient discreetness for some, and may also be undesirable either or both from an associated psychological stigma or from physical discomfort.

Due to these and other problems and disadvantages encountered in the prior art, a need exists for an improved feminine sanitary device that facilitates and enhances protection, especially when the user is reclining or lying down.

SUMMARY OF THE INVENTION

The present invention solves the above-identified and other problems and disadvantages in the prior art by providing a contoured and shaped feminine sanitary device for facilitating and enhancing fluid absorption in certain areas and during certain activities. More specifically, the device provides significantly improved protection over the prior art, particularly when the user assumes non-vertical positions, such as, for example, when reclining or laying in a prone, supine, or side position.

Preferably, the device comprises an elongated body including a central portion, a back extension, a front extension, one or more raised areas, and one or more wings. The central portion is substantially elongated and rectangular in shape and adapted for placement against the female genital area in much the same manner as a prior art pad. The back extension is connected to or otherwise extends substantially continuously from a rearward end of the central portion, presents additional surface area, and is adapted for placement against the user's lower buttock area to absorb at least some of any fluid that may avoid absorption by the central portion and flow rearward along bodily contours into this lower buttock area such as when the user is in a substantially supine position. The front extension is connected to or otherwise extends substantially continuously from a forward end of the central portion, also presents additional surface area, and is adapted for placement against the user's pelvic or lower abdominal area to absorb at least some of any fluid that may avoid absorption by the central portion and flow forwardly along bodily contours when the user is in a substantially prone position. The extensions may be given substantially any suitable simple or complex shape as well as relief features for more closely accommodating the user's legs or other body parts. Securement mechanisms may be provided for one or more of the central portion or back or front extensions in order to aid in maintaining the portion or area in its proper operating position.

The one or more raised areas are located on the body of the device in areas where fluid flow is likely to occur, and have a raised shape, such as a rounded swelling or even, as appropriate, a wedge, that results in more certain and sustained contact with the user's body and therefore better protection. There may be any one or more of three such areas: a vaginal area, a rear area, and a front area. The vaginal area is located in a center area of the central portion; the rear area is located rearwardly of the vaginal area, such as near the intersection of the central portion and the back extension where the human body forms a natural crevice and intersection for fluid flowing rearwardly along bodily contours; and the front area is located forwardly of the vaginal area, such as near the intersection of the central portion and the front extension to intercept fluid flowing forwardly along bodily contours. The raised areas are preferably constructed of a material or materials and in such a manner that fluid absorbed by the raised areas is able or even encouraged to migrate into adjacent areas of the device so as to slow or avoid substantial or complete saturation of the raised areas which might diminish or preclude further absorption and thereby diminish or preclude further performance or operation of the device.

Thus, it will be appreciated that the feminine sanitary device of the present invention provides a number of substantial advantages over the prior art, including, for example, providing significantly improved protection, particularly when the user assumes non-vertical positions, such as, for example, when reclining or laying in a prone, supine, or side position. In particular, the oversized and appropriately shaped back and front extensions provide greater protection against fluid not absorbed by the central portion, and the appropriately located raised areas further improve protection.

These and other features of the present invention are described in greater detail in the section entitled DETAILED DESCRIPTION OF A PREFERRED EMBODIMENT, set forth below.

BRIEF DESCRIPTION OF THE DRAWINGS

A preferred embodiment of the present invention is described in detail below with reference to the attached drawing figures, wherein.

DETAILED DESCRIPTION OF THE PREFERRED EMBODIMENT

With reference to the figures, a feminine sanitary device 10 is described, shown, and otherwise disclosed herein in accordance with one or more preferred embodiments of the present invention. The device 10 of the present invention provides substantially improved protection over the prior art, particularly when the user assumes non-vertical positions, such as, for example, when reclining or laying in a prone, supine, or side position.

Figure 3A:
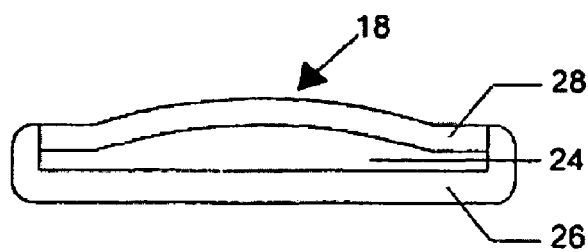
FIG. 3a is a first cross-sectional view along line A-A of the feminine sanitary device of FIG. 1 showing a contemplated first possible thickness of a raised area of the device.
Figure 3B:
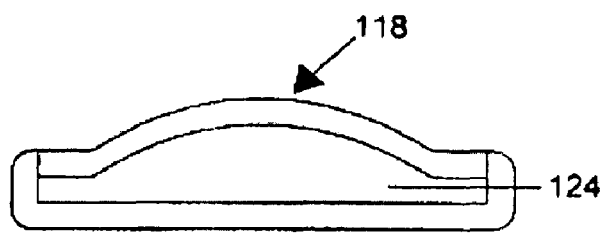
FIG. 3b is a second cross-sectional view along line A-A of the feminine sanitary device of FIG. 1 showing a contemplated second possible thickness of the raised area of the device.

Preferably, the device 10 broadly comprises an elongated body including a central portion 12, a back extension 14, a front extension 16, one or more raised areas 18, and one or more wings 20. Referring particularly to FIGS. 3a and 3b, the body includes a substantially fluid-absorbent core 24 interposed between a substantially fluid-impermeable backing 26 and a substantially fluid permeable cover 28 for absorbing and retaining fluid. This cross-sectional construction is generally substantially consistent over the entire body, including the central portion and the extensions.

The central portion 12 is substantially elongated and rectangular in shape and adapted for placement against the female genital area in much the same manner as a prior art pad.

Figure 1:
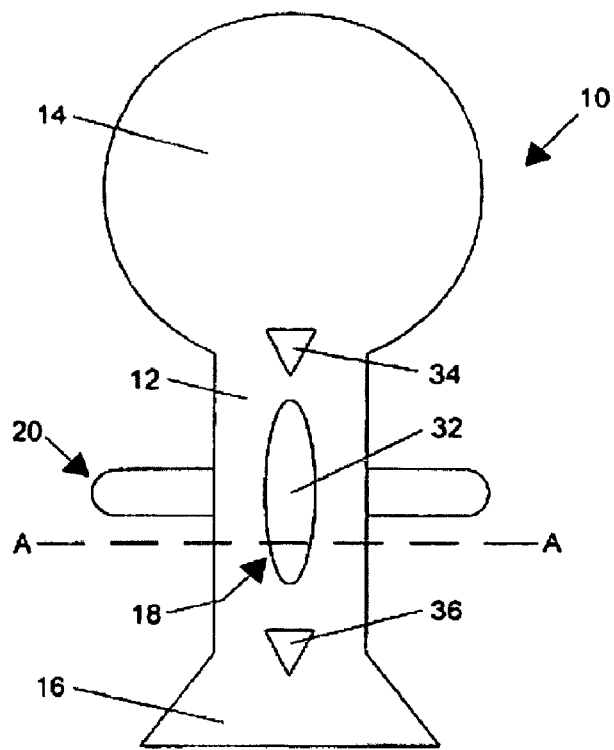
FIG. 1 is a plan view of a preferred first embodiment of the feminine sanitary device of the present invention.
Figure 2:
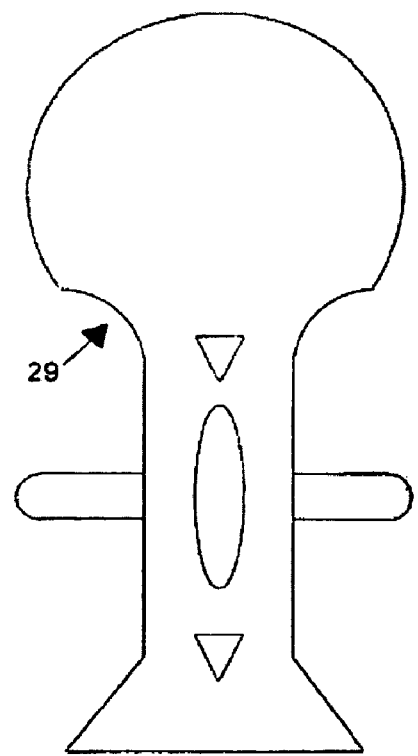
FIG. 2 is a plan view of a preferred second embodiment of the feminine sanitary device of the present invention.

The back extension 14 is connected to or otherwise extends substantially continuously from a rearward end of the central portion 12, presents additional surface area, and is adapted for placement against the user's lower buttock area to absorb at least some of any fluid that may avoid absorption by the central portion 12 and flow rearward along bodily contours into this lower buttock area such as when the user is in a substantially supine position. The back extension 14 may have substantially any suitable simple shape, (as shown in FIG. 1) such as round or triangular, or complex shape (as shown in FIG. 2), such as round or triangular with appropriately shaped scallops, cut-outs, or other relief features 29 to more closely accommodate the user's legs or other body parts.

The front extension 16 is connected to or otherwise extends substantially continuously from a forward end of the central portion 12, also presents additional surface area, and is adapted for placement against the user's pelvic or lower abdominal area to absorb at least some of any fluid that may avoid absorption by the central portion 12 and flow forwardly along bodily contours when the user is in a substantially prone position. The front extension 16 may be given substantially any suitable simple shape, such as round or triangular, or complex shape, such as round or triangular with appropriately shaped scallops, cut-outs, or other relief features similar to those shown in FIG. 2 to more closely accommodate the user's legs or other body parts.

Figure 4:
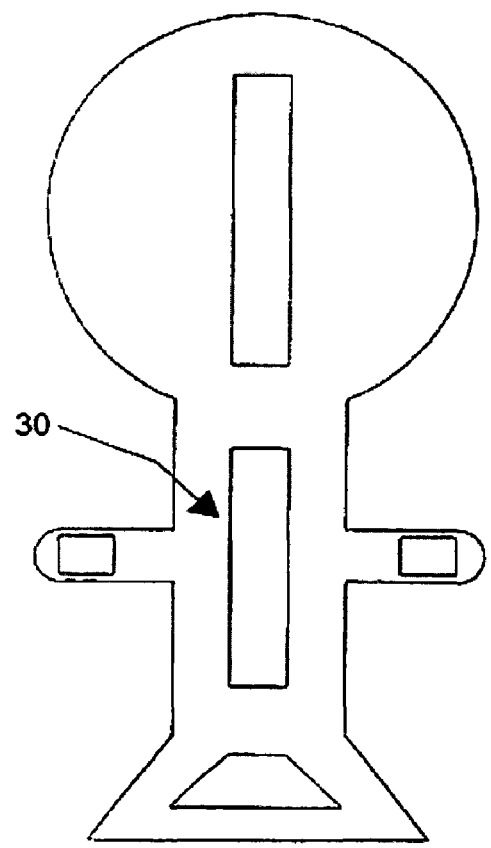
FIG. 4 is a bottom view of the feminine sanitary device of FIG. 1.

Referring particularly to FIG. 4, securement mechanisms 30 may be provided for one or more of the central portion 12, back extension 14, or front extension 16 in order to aid in maintaining the portion or area in its proper operating position. Such securement mechanisms 30 may take the form of adhesive or hook-and-loop tape associated with a backside of the device 10 for removably securing it to an undergarment worn by the user. Such securement mechanisms 30 may supplement or replace the one or more wings 20 which are discussed below.

Referring particularly to FIGS. 3a and 3b, the one or more raised areas 18 are located on the body in areas where fluid flow is likely to occur. While the fluid-absorbent core 24 extends substantially throughout the entire body, the areas 18 provide even greater absorbing ability or capacity. This enhanced ability or capacity of the areas 18 may be achieved either by use of a different and even more absorbent material than the super-absorbent core material, by use of additional thicknesses of the core or other material, or by any combination thereof to achieve the desired characteristic. Such additional thicknesses of material provide a raised shape, such as a rounded swelling or even, as appropriate, a wedge, that results in more certain and sustained contact with the user's body and therefore better protection. As shown in FIGS. 3*a* and 3*b*, the height of the raised areas 18,118 may vary from approximately between 0.25 inch to 1.0 inch based on a variety of factors, including, for example, desired absorbing capacity. The raised area 118 of FIG. 3*b* is substantially higher than the raised area 18 of FIG. 3*a*, potentially allowing the raised area 118 of FIG. 3*b* to both maintain closer contact with the user's body and provide greater absorbing capacity due to its greater amount of absorbent core material 124. It is contemplated that there may be any one or more of three such areas 18: a vaginal area 32, a rear area 34, and a front area 36. The vaginal area 32 may be provided with an appropriate shape, such as an elongated elliptical shape, and positioned in a center area of the central portion 12. The rear area 34 may be provided with an appropriate shape, such as a triangular shape, and positioned rearwardly of the vaginal area 32, such as near the intersection of the central portion 12 and the back extension 14 where the human body forms a natural crevice and intersection for fluid flowing rearwardly along bodily contours. The front area 36 may be provided with an appropriate shape, such as a triangular shape, and positioned forwardly of the vaginal area 32, such as near the intersection of the central portion 12 and the front extension 16 to intercept fluid flowing forwardly along bodily contours. It is contemplated that the areas may be of equal, differing, or even varying height depending on the desired performance characteristics at that location. The raised areas 18 are preferably constructed of a material or materials and in such a manner that fluid absorbed by the raised areas 18 is able or even encouraged to migrate into adjacent areas of the device 10 so as to slow or avoid substantial or complete saturation of the raised areas 18 which might diminish or preclude further absorption and thereby diminish or preclude further performance or operation of the device 10.

The one or more wings 20 project outwardly perpendicularly from the central portion 12 of the body and function both to provide protection against fluid flowing sidewardly and to facilitate maintaining the device 10 in its proper operating position. Preferably, one wing projects outwardly from each side of the central portion 12, has some absorbent ability, and includes a securement mechanism, such as described above, to allow for securing the body to the undergarment worn by the user in an otherwise substantially conventional manner.

From the preceding description, it will be appreciated that the feminine sanitary device of the present invention provides a number of substantial advantages over the prior art, including, for example, providing significantly improved protection, particularly when the user assumes non-vertical positions, such as, for example, when reclining or laying in a prone, supine, or side position. In particular, the oversized and appropriately shaped back and front extensions provide greater protection against fluid not absorbed by the central portion, and the appropriately located raised areas further improve protection.

Although the invention has been described with reference to the preferred embodiments illustrated in the attached drawings, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A feminine sanitary device comprising:
    a body having a substantially fluid-absorbing core interposed between a substantially fluid-impermeable backing and a substantially fluid-permeable cover for absorbing bodily fluid, the body comprising:
        an oversized front extension;
        an oversized back extension; and
        a central portion, adapted for placement against a female genital area, having two sides, a front edge integrally connected to the front extension and a back edge integrally connected to the back extension;
    a first raised area located in the central portion for absorbing and directing fluid, the first raised area having a longitudinal axis positioned substantially equidistant from the sides of the central portion;
    a second raised area located in the front extension for directing the bodily fluid;
    a third raised area located in the back extension for directing the bodily fluid;
    wherein the oversized front and back extensions provide protection against fluid unabsorbed by the central portion;
    wherein a longitudinal area located between the vaginal raised area and the back raised area is non-raided; and
    wherein a longitudinal area located between the vaginal raised area and the front raised area is non-raised.

2. A feminine sanitary device comprising:
    a body having a substantially fluid-absorbing core interposed between a substantially fluid-impermeable backing and a substantially fluid-permeable cover for absorbing bodily fluid, the body comprising:
        a front extension;
        a back extension; and
        a central portion, adapted for placement against a female genital area, having two sides, a front edge integrally connected to the front extension and a back edge integrally connected to the back extension;
    a vaginal raised area located in the central portion for absorbing and directing fluid, the vaginal raised area having a longitudinal axis positioned substantially equidistant from the sides of the central portion;
    a front raised area located forwardly of the vaginal area at an intersection of the central portion and the front extension; and
    a back raised area located rearwardly of the vaginal area at an intersection of the central portion and the back extension;
    wherein a longitudinal area located between the vaginal raised area and the back raised area is non-raised; and
    wherein a longitudinal area located between the vaginal raised area and the front raised area is non-raised.

3. The feminine sanitary device of claim 2, wherein the front raised area and the back raised area are substantially triangular shaped.

4. The feminine sanitary device of claim 2, wherein the vaginal raised area is approximately between 0.25 inch and 1.00 inch in height relative to non-raised areas.

5. The feminine sanitary device of claim 2, further comprising one or more wings connected to and projecting perpendicularly from the sides of the central portion and being sufficiently flexible to wrap around a portion of an undergarment worn by a user to aid in retaining the feminine sanitary device in its proper operating position.

6. The feminine sanitary device of claim 2, further comprising one or more securement mechanisms on a backside portion of the body for securing the feminine sanitary device to an undergarment worn by a user to aid in retaining the feminine sanitary device in its proper operating position.

7. The feminine sanitary device of claim 2, wherein the vaginal raised area and the back raised area are different heights.

8. The feminine sanitary device of claim 2, wherein the vaginal raised area and the back raised area are the same height.

9. The feminine sanitary device of claim 2, wherein the vaginal raised area and the front raised area are different heights.

10. The feminine sanitary device of claim 2, wherein the vaginal raised area and the front raised area are the same height.

11. A feminine sanitary device comprising:
a body having a substantially fluid-absorbing core interposed between a substantially fluid-impermeable backing and a substantially fluid-permeable cover for absorbing bodily fluid, the body comprising:
  a front extension;
  a back extension; and
  a central portion, adapted for placement against a female genital area, having two sides, a front edge integrally connected to the front extension and a back edge integrally connected to the rear extension;
a vaginal raised area located in the central portion for absorbing and directing fluid, the vaginal raised area having a longitudinal axis positioned substantially equidistant from the sides of the central portion;
a front raised area located forwardly of the vaginal area at an intersection of the central portion and the front extension; and
a back raised area located rearwardly of the vaginal area at an intersection of the central portion and the back extension;
wherein a longitudinal area located between the vaginal raised area and the back raised area is non-raised; and
wherein a longitudinal area located between the vaginal raised area and the front raised area is non-raised.

12. The feminine sanitary device of claim 11, wherein the front raised area and the back raised area are substantially triangular shaped.

13. The feminine sanitary device of claim 11, wherein the two sides of the control portion are non-raised.

14. The feminine sanitary device of claim 11, further comprising one or more wings connected to and projecting perpendicularly from the sides of the central portion and being sufficiently flexible to wrap around a portion of an undergarment worn by a user to aid in retaining the feminine sanitary device in its proper operating position.

15. The feminine sanitary device of claim 11, wherein the front raised area and the back raised area are centered along the longitudinal axis of the vaginal raised area.

16. The feminine sanitary device of claim 11, wherein the vaginal raised area and the back raised area are different heights.

17. The feminine sanitary device of claim 11, wherein the vaginal raised area and the back raised area are the same height.

* * * * *